(12) United States Patent
Cavazza et al.

(10) Patent No.: US 6,696,492 B1
(45) Date of Patent: Feb. 24, 2004

(54) USE OF L CARNITINE AND ITS ALKANOYL DERVATIVES FOR THE PREPARATION OF A MEDICAMENT USEFUL FOR THE TREATMENT OF PATIENTS SUFFERING FROM DIABETIC AND/OR DYSMETABOLIC NEPHROPATHY

(75) Inventors: Claudio Cavazza, Rome (IT); Giovanni Valentini, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/019,627

(22) PCT Filed: Jul. 12, 2000

(86) PCT No.: PCT/IT00/00288

§ 371 (c)(1),
(2), (4) Date: Jan. 3, 2002

(87) PCT Pub. No.: WO01/07038

PCT Pub. Date: Feb. 1, 2001

(30) Foreign Application Priority Data

Jul. 27, 1999 (IT) .................................... RM99A0480

(51) Int. Cl.⁷ ............................................. A61K 31/205
(52) U.S. Cl. ...................................................... 514/556
(58) Field of Search .......................................... 514/556

(56) References Cited

U.S. PATENT DOCUMENTS

| 4,255,449 | A | * | 3/1981 | Cavazza | 424/316 |
| 4,362,719 | A | * | 12/1982 | Cavazza | 424/316 |
| 4,751,242 | A | * | 6/1988 | Calvani et al. | 514/554 |
| 5,614,224 | A | * | 3/1997 | Womack | 424/646 |
| 6,328,998 | B1 | * | 12/2001 | Cavazza | 424/725 |
| 6,335,369 | B1 | * | 1/2002 | Cavazza | 514/561 |
| 6,429,230 | B1 | * | 8/2002 | Cavazza | 514/561 |

FOREIGN PATENT DOCUMENTS

| WO | 98 01128 A | 1/1998 |
| WO | 98 33494 A | 8/1998 |
| WO | 99 06039 A | 2/1999 |

OTHER PUBLICATIONS

Boehles H et al; "The Influence of L Carnitine Supplementation on Lipid Metabolism in Rrenal Insufficient Children on Hemodialysis"; Infusionstherapie; vol. 18, No. 5; 1991; pp. 224–226; XP001011523.

* cited by examiner

Primary Examiner—Kevin E. Weddington
(74) Attorney, Agent, or Firm—Nixon & Vanderhye P.C.

(57) ABSTRACT

Patients suffering from diabetic and/or dysmetabolic nephropathy are treated with L-carnitine or its alkanoyl derivatives.

5 Claims, No Drawings

USE OF L CARNITINE AND ITS ALKANOYL DERVATIVES FOR THE PREPARATION OF A MEDICAMENT USEFUL FOR THE TREATMENT OF PATIENTS SUFFERING FROM DIABETIC AND/OR DYSMETABOLIC NEPHROPATHY

This application is the US national phase of international application PCT/ITT00/00288 filed Jul. 12, 2000, which designated the US.

The invention described herein relates to the use of L-carnitine and its alkanoyl derivatives, optionally in the form of a pharmaceutically acceptable salt, for the preparation of a medicament which is useful for the treatment of patients suffering from diabetic and/or dysmetabolic nephropathy.

BACKGROUND OF THE INVENTION

Nephropathy caused by glomerular damage not strictly related to an immunological cause (autoimmune disease) or to glomerulonephritis is today one of the most frequent causes of chronic kidney failure and subsequent terminal uraemia. In Western society, 30–35% of patients undergoing dialysis have had a diagnosis of nephropathy due to dysmetabolism which has reduced and eventually abolished their renal function.

The first signs of such disease are manifested a number of years after the onset of diabetes mellitus and/or hyperlipidaemia and consist in the presence of microalbuminuria (presence of abnormal excretion of albumin quantified in amounts ranging from 30 to 300 mg in 24-hour urine samples), which is an unmistakable sign of damage at the level of the renal glomerular filtration barrier.

The earliest morphological abnormalities of the nephropathy consist in a thinning of the glomerular basal membrane and an increase in the mesangial component due to an accumulation of extracellular matrix. This accumulation of glomerular matrix is the main cause of a reduced nutrient and oxygen supply capacity at the level of the glomerular wall and, as a final event, leads to glomerulosclerosis and the loss of filtering capacity on the part of the glomerule. The residual glomerules adapt to the need to purify and regulate the reabsorption of liquids and salts via a glomerular hyperfiltration and hypertension mechanism, not so much directly associated with an actual state of systemic arterial hypertension, but denoting rather an organ disease. This adaptation, however, leads to an increase in glomerulosclerosis and to a subsequent further reduction in the residual function of the glomerules. At this stage, the arteriolar hypertension at precapillary level is a stimulus for enhancing the glomerulosclerosis. The renal vascular system shows typical signs of widespread atherosclerosis, often complicated by the presence of a frank associated lipidaemia. In fact, non-enzymatic glycosylation of lipoproteins may speed up the atherosclerotic phenomenon. The presence of HDL and antioxidant substances in these conditions may exert an antiatherogenic action. In conditions of hyperglycaemia there is also increased secretion of endothelin-1 as well as a reduction of nitrous oxide release by the endothelium.

The aim of the therapy currently available is to delay the progression of the nephropathy by means of dietetic and pharmacological control of the hyperglycaemia and/or dyslipidaemia, sometimes in combination with the use of calcium antagonists and/or ACE inhibitors which are useful for reducing systemic and glomerular blood pressure. Despite all the therapeutic measures currently available, the present expectancy for maintaining minimal renal functional capability is not more than 5 to 10 years. The patients suffering from this condition are in any event destined to develop terminal chronic kidney failure in this time period, requiring dialysis-type replacement treatment or a kidney transplant.

It is clear that the present situation entails progressive deterioration of the quality of life of the patient, whose prospects of entering into dialysis treatment or, even worse, of facing a kidney transplant, with all the attendant problems of having to wait for an available organ, and, in any case, the prospect of having to undergo complex transplant surgery, with its known consequences, make it highly desirable to find a solution which the present state of the art is unable to offer. In particular, a medicament capable at least of delaying, if not of resolving, the condition of terminal uraemia of patients suffering from chronic kidney failure is highly desirable.

Propionyl L-carnitine is known to exert a protective action on the endothelial cells and, in previous organ ischaemia and reperfusion experiments, has been found to be capable of reducing the damage induced by the ischaemia (Di Silverio et al., Acta Urol. Ital., 1993, (I), 71–75). This latter study, however, only shows the ability of propionyl L-carnitine to reduce acute postoperative ischaemic damage in patients with kidney stones and chronic kidney failure.

Propionyl L-carnitine is also capable of improving the oxidative metabolism of myocardial and skeletal muscle cells subjected to a reduced blood supply.

It has also been recently demonstrated in studies conducted in animals that the administration of propionyl L-carnitine is capable of improving the functional capability and perfusion of the peripheral nerves in rats in which a diabetic state was induced by the administration of streptozocin (Hotta et al., The Journal of Pharmacology and Experimental Therapeutics, 276:49–55, 1996).

Moreover, again in rats in which a diabetic state was induced by the administration of streptozocin, it has been demonstrated that the high plasma lipid levels (total cholesterol, triglycerides, LDL) as a result of the lipid dysmetabolism induced by the diabetic state are reduced by treatment with propionyl L-carnitine.

It has now surprisingly been found that L-carnitine and its lower alkanoyl derivatives have a thoroughly unexpected action in terms of functional recovery in patients suffering from chronic diabetic and/or dysmetabolic nephropathy.

ABSTRACT OF THE INVENTION

One subject of the invention described herein is the use of L-carnitine and its lower alkanoyl derivatives, where what is meant by lower alkanoyl derivative is a straight or branched aliphatic acyl residue with from 2 to 8 carbon atoms, optionally in the form of a pharmaceutically acceptable salt for the preparation of a medicament useful for the treatment of patients suffering from diabetic and/or dysmetabolic nephropathy.

L-carnitine and its lower alkanoyl derivates are well known for various therapeutic uses. In particular, U.S. Pat. No. 4,327,167, in the name of the applicant, describes the use of alkanoyl carnitines, as understood here above, in a therapeutic method for the treatment of chronic uraemic patients undergoing regular dialysis. Polysaline solutions for haemodialysis containing an alkanoyl carnitine have also been described. European patent EP 0793962, in the name of the applicant, describes the use of propionyl L-carnitine for the preparation of a medicament useful for the selective treatment of chronic obliterating atherosclerosis (intermittent claudication). Italian patent IT 1155772, taken out in the name of the applicant, describes the use of alkanoyl L-carnitine in the therapy of myocardial anoxia, ischaemia, arrhythmia syndromes and heart failure. U.S. Pat. 4,255,449, issued in the name of the applicant, described the use of L-carnitine in the treatment of dyslipidaemias. Patent application WO99/06039, filed in the name of the applicant, describes the use of L-carnitine and its alkanoyl derivatives in combination with polycosanols for the treatment of dyslipidaemias.

WO 98/01128 discloses the use of alkaanoyl L-carnitines for the therapeutic treatment of diseases related to IGF-1.

Among the pathologies mentioned in WO 98/01128 type-II diabetes or ischemic damage at the renal level are mentioned.

WO 98/33494 discloses compositions useful for the treatment and prevention of diabetic complications associated with microangiopathy, such as nephropathy.

WO 98/33494 discloses that decreased L-carnitine levels are common in insulin dependent diabetics and that carnitine supplementation reduces serum triglycerides.

In Infusionstherapie October 1991;18(5):224-6 is reported that the use of L-carnitine, in renally insufficient children, reduces the serum triglyceride levels and that L-carnitine is an antiatherogenic compound.

In the above cited publications there is no suggestion how to use L-carnitine or alkanoyl L-carnitines for treating diabetic and/or dysmetabolic nephropathy, as taught in the present application.

There are also numerous descriptions of L-carnitine and its alkanoyl derivatives in combination with other active ingredients, such as, for example, gamma-linolenic acid. (see WO98/41113), for the treatment and prevention of the adverse effects of diabetes mellitus, particularly peripheral neuropathy.

DETAILED DESCRIPTION OF THE INVENTION

What is meant by a lower alkanoyl is an acyl residue with from 2 to 8 carbon atoms, and preferably from 2 to 6, such as acetyl, propionyl, butyryl, isobutyryl, valeryl, isovaleryl. 2-methylbutyryl, 2,2-dimethylpropionyl, hexanoyl, heptanoyl, octanoyl and all their possible isomers.

What is meant by pharmacologically acceptable salt of L-carnitine or alkanoyl L-carnitine is any salt of these with an acid that does not give rise to unwanted toxic or side effects. Such acids are well known to pharmacologists and to experts in pharmaceutical technology.

Examples of pharmacologically acceptable salts of L-carnitine or alkanoyl L-carnitines, though not exclusively these, are: chloride; bromide; orotate; acid aspartate; acid citrate; acid phosphate; fumarate and acid fumarate; maleate and acid maleate; acid oxalate; acid sulphate; glucose phosphate; tartrate and acid tartrate.

The medicament prepared according to the invention described herein will be administered in the form of a pharmaceutical composition that can be prepared according to the common knowledge of experts in the field.

According to the particular administration route selected—oral, parenteral or intravenous—the pharmaceutical composition will have an appropriate form.

Examples of pharmaceutical compositions, in which the medicament according to the invention is present, are solid or liquid oral forms, such as tablets, capsules of all kinds, pills, solutions, suspensions, emulsions in the form of unit or divided doses, syrups, and drinkable unit dosage forms ready for use or extempore. Other examples are the parenteral forms, the intramuscular, subcutaneous or intravenous injectable forms. Controlled- or programmed-release forms can also be supplied.

The dosages, posology and therapeutic regimen in general will be determined by the primary care physician according to his or her knowledge, the patient's condition and the extent and severity of the disease to be treated.

Combinations of L-carnitine and one of its alkanoyl derivatives as defined above, or with additional active ingredients, are envisaged, even in the same medicament or in the form of therapeutic kits containing instructions for the simultaneous or sequential administration of the active ingredients according to a planned regimen.

In a first preferred realisation, the invention described herein contains propionyl L-carnitine (PLC).

For the purposes of impeding or delaying the deterioration of kidney function as long as possible, it has surprisingly been demonstrated that the administration of L-carnitine, or of one of its alkanoyl derivatives, as defined above, particularly propionyl L-carnitine, is capable of reducing organ damage at the level of the renal glomerules induced by the dysmetabolic disease, thus delaying the entry of the preterminal uraemic patient into dialysis, or even the need for kidney transplantation. The advantage of the invention described herein is clear in terms of the patient's quality of life, the cost of dialysis therapy or, in the more severe cases, waiting for the availability of organs for transplantation.

The use of propionyl L-carnitine in this pathology has also been shown to be devoid of major side effects in man, when administered to patients suffering from diabetes mellitus and peripheral arteriopathy. In such patients no severe unwanted effects have been recorded during 6 months' treatment.

DETAILED DESCRIPTION OF THE INVENTION

The invention will be described, also by means of examples, in its preferred realisation form, that is to say with the use of propionyl L-carnitine (hereinafter referred to using the abbreviation PLC).

The following examples further illustrate the invention.

EXAMPLE 1

A clinical physiology study was conducted in human subjects for the purpose of establishing whether PLC was also capable of exerting a vasodilating action at the microcirculatory level. Exertion of such action would, in fact, be capable of improving blood supply in areas where, as a result of organ disease, a state of chronic blood flow reduction may be created, as occurs, for instance, at renal glomerule level in diabetic nephropathy. This study was conducted in 6 healthy volunteers, whose overall blood flow was measured by plethysmography in the forearm, both in basal conditions and after 60-minute intravenous infusion of PLC at the dose of 12 micrograms per minute. The choice of dose to be administered was based on kinetics calculations, in order to try and achieve a steady state plasma concentration of PLC similar to the one obtained with chronic oral administration of 2 grams of PLC.

The results of this study show that the administration of PLC induces an approximately 25% increase in blood flow as compared to resting basal flow.

EXAMPLE 2

A further clinical study again conducted in healthy volunteers (8 subjects) with the same methodology described above and with local intra-arterial administration of PLC has confirmed the vasodilatory action of this drug. Furthermore, in this latter study, after blood flow estimation 3 minutes after infusion of PLC, nitro-L-arginine was administered for the purposes of assessing whether this vasodilatory effect was due to release of nitrous oxide by the endothelium. The concomitant administration of PLC and nitro-L-arginine brought about a more than 50% reduction in the vasodilatation previously induced by the administration of PLC alone, thereby confirming that, by inhibiting the release of nitrous oxide by the endothelial wall through the action of nitro-L-arginine, the PLC-induced vasodilatory effect is substantially reduced.

EXAMPLE 3

Lastly, a clinical pilot study has been conducted in a small patient sample, consisting of 8 patients suffering from type 2 diabetes mellitus and diabetic nephropathy in the microalbuminuria stage without evidence of frank renal insufficiency and 10 patients suffering from type 2 diabetes mellitus and renal insufficiency (serum creatinine>2 mg/dl and creatinine clearance <40 ml/min).

Both patient groups were treated with 1.5 grams/day of PLC administered in three distinct doses of 500 mg at three different times of day (1 tablet after breakfast, lunch and dinner) for a total period of 6 months.

In the group suffering from microalbuminuria without evidence of frank renal insufficiency, a statistically significant reduction in the urinary microalbumin excretion rate from $37.8\pm4.6$ mg/g creatinine to $21.3\pm5.1$ mg/g creatinine ($p<0.01$) was found after 6 months' treatment. This patient group had been observed for three months before starting treatment with PLC and the microalbuminuria levels had remained practically unchanged throughout this period, thus showing a basal stability of this variable. In the second group of patients suffering from diabetic nephropathy and dyslipidaemia, after 6 months' treatment a significant reduction was found in 24-h proteinuria which dropped from $6.2\pm2.3$ g/24 h to $3.1\pm1.2$ g/24 h ($p<0.01$). In addition, creatinine clearance rose from 34.6 ml/min$\pm$4.6 to 42.7 ml/min$\pm$7.3. Finally, as regards the lipid pattern, a reduction in triglycerides was observed from $217\pm75$ mg/dl to $192\pm62$ mg/dl and in LDL from $169\pm15$ mg/dl to $158\pm10$ mg/dl.

The results of these experiments demonstrate that PLC plays an active role in protecting the kidney against organ damage, with a reduction in pressure stress at the microcirculatory and probably at the renal glomerule level, reducing the organ damage related to atherosclerosis and chronic hypoxia. It also induces an improvement in renal functional capability in subjects suffering from dysmetabolic nephropathy and is therefore effective in reducing the deterioration of kidney function which leads to terminal chronic kidney failure in these patients.

What is claimed is:

1. A method of treating a patient suffering from diabetic and/or dysmetabolic nephropathy comprising administering to the patient L-carnitine or its alkanoyl derivative, in which the alkanoyl is a straight or branched aliphatic residue with from 2 to 8 carbon atoms, or in the form of a pharmaceutically acceptable salt.

2. The method according to claim 1, in which the alkanoyl L-carnitine is propionyl L-carnitine.

3. The method according to claim 1, in which deterioration of kidney function is impeded or retarded.

4. The method according to claim 3, in which the need for dialytic replacement treatment or for an organ transplant is delayed.

5. The method according to claim 4, in which organ damage induced by the dysmetabolic disease is reduced at the renal glomerule level.

* * * * *